US007245971B2

(12) United States Patent
Park et al.

(10) Patent No.: US 7,245,971 B2
(45) Date of Patent: *Jul. 17, 2007

(54) SYSTEM AND METHOD FOR APPLYING THERAPY DURING HYPERPNEA PHASE OF PERIODIC BREATHING USING AN IMPLANTABLE MEDICAL DEVICE

(75) Inventors: Euljoon Park, Valencia, CA (US); Michael Benser, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 335 days.

This patent is subject to a terminal disclaimer.

(21) Appl. No.: 10/829,719

(22) Filed: Apr. 21, 2004

(65) Prior Publication Data
US 2005/0240240 A1    Oct. 27, 2005

(51) Int. Cl.
*A61N 1/36* (2006.01)
(52) U.S. Cl. ........................................ 607/42; 600/529
(58) Field of Classification Search ............... 600/534, 600/532, 484, 529; 607/42
See application file for complete search history.

(56) References Cited

U.S. PATENT DOCUMENTS

| 5,056,519 | A |   | 10/1991 | Vince ..................... 128/419 G |
|---|---|---|---|---|
| 5,215,082 | A | * | 6/1993  | Kallok et al. ................. 607/42 |
| 5,265,604 | A | * | 11/1993 | Vince ........................... 607/42 |
| 5,755,750 | A |   | 5/1998  | Petruska et al. ............... 607/75 |
| 5,861,022 | A |   | 1/1999  | Hipskind ..................... 607/107 |
| 5,911,218 | A |   | 6/1999  | DiMarco ................ 128/200.24 |
| 6,064,910 | A |   | 5/2000  | Andersson et al. ............ 607/20 |
| 6,132,384 | A |   | 10/2000 | Christopherson et al. ... 600/529 |
| 6,415,183 | B1 |  | 7/2002  | Scheiner et al. ............... 607/42 |
| 6,589,188 | B1 |  | 7/2003  | Street et al. .................. 600/538 |
| 6,600,949 | B1 |  | 7/2003  | Turcott ........................ 600/518 |
| 6,641,542 | B2 |  | 11/2003 | Cho et al. .................... 600/529 |
| 2002/0099256 | A1 | | 7/2002 | Manne ........................... 600/9 |
| 2002/0177882 | A1 | | 11/2002 | DiLorenzo .................... 607/45 |
| 2003/0045914 | A1 | | 3/2003 | Cohen et al. .................. 607/62 |
| 2003/0078619 | A1 | | 4/2003 | Bonnet et al. .................. 607/4 |
| 2003/0216792 | A1 | | 11/2003 | Levin et al. ................... 607/48 |

FOREIGN PATENT DOCUMENTS

WO   WO 93/02744        2/1993
WO   WO 01/41868 A1     6/2001

* cited by examiner

*Primary Examiner*—George R. Evanisko
*Assistant Examiner*—Rex Holmes

(57) ABSTRACT

Techniques are provided for treating periodic breathing, such as Cheyne-Stokes Respiration, using an implantable medical system. In one technique, diaphragmatic stimulation is delivered during a hyperpnea phase of periodic breathing via electrical stimulation of the phrenic nerves. Diaphragmatic stimulation is synchronized with intrinsic inspiration so as to increase the amplitude of diaphragmatic contraction during inspiration. This tends to decrease intrathoracic pressure leading to occlusion of the respiratory airway. Occlusion reduces actual ventilation during hyperpnea, thus reducing the cyclic blood chemistry imbalance that sustains periodic breathing so as to either mitigate periodic breathing or eliminate it completely. In another technique, respiration is instead inhibited during the hyperpnea phase of periodic breathing by blocking phrenic nerve signals to the extent necessary to reduce ventilation to terminate periodic breathing or at least mitigate its severity. Techniques are also described for controlling the type of therapy applied in response to periodic breathing.

16 Claims, 9 Drawing Sheets

SYSTEM AND METHOD FOR APPLYING THERAPY DURING HYPERPNEA PHASE OF PERIODIC BREATHING USING AN IMPLANTABLE MEDICAL DEVICE

CROSS REFERENCE TO RELATED APPLICATIONS

This application is related to U.S. patent application Ser. No. 10/830,357, titled "System and Method for Applying Therapy During Hyperpnea Phase of Periodic Breathing Using an Implantable Medical Device", filed Apr. 21, 2004, now U.S. Pat. No. 7,082,331.

FIELD OF THE INVENTION

The invention generally relates to implantable medical devices, such as pacemakers and implantable cardioverter/defibrillators (ICDs), and in particular, to techniques for treating periodic breathing within a patient in which such a medical device is implanted.

BACKGROUND OF THE INVENTION

Periodic breathing refers to abnormal respiration patterns that alternate between hypopnea (i.e. diminished breathing) and hyperpnea (i.e. fast, deep breathing.) One form of periodic breathing is Cheyne-Stokes Respiration (CSR), which can occur in patients with congestive heart failure (CHF). Briefly, CSR arises principally due to a time lag between blood carbon dioxide ($CO_2$) levels sensed by the central nervous system and the blood $CO_2$ levels. With CHF, poor cardiac function results in poor blood flow to the brain such that the central nervous system responds to blood $CO_2$ levels that are no longer properly representative of the overall blood $CO_2$ levels in the body. Hence, the central nervous system triggers an increase in the depth and frequency of breathing in an attempt to compensate for perceived high blood $CO_2$ levels whereas the blood $CO_2$ levels have already dropped. By the time the central nervous system detects the drop in blood $CO_2$ levels and slows respiration in response, the blood $CO_2$ levels have already increased. This cycle becomes increasingly unbalanced until respiration periodically alternates between hypopnea (or hypoventilation) and hyperpnea (or hyperventilation). The wildly fluctuating blood chemistry levels can exacerbate CHF and other medical conditions. Moreover, the periods of hypopnea can be sufficiently pronounced that no breathing occurs, i.e. the patient suffers from episodes of frank apnea. The episodes of apnea can last so long that the patient, if sleeping, is awakened due to increasingly high blood $CO_2$ levels. Arousal from sleep usually lasts only a few seconds, but even brief arousals nevertheless disrupt continuous sleep and can prevent the patient from achieving rapid eye movement (REM) sleep, which is needed.

Another form of periodic breathing can arise due to central sleep apnea (CSA), which is a neurogenic sleep disorder. When blood $CO_2$ levels exceed a certain threshold, the central nervous system should generate a burst of nerve signals for triggering inspiration. The nerve signals are relayed via phrenic nerves to the diaphragm and via other nerves to chest wall muscles, which collectively contract to expand the lungs. With CSA, however, the nerve signals are not properly generated at times while the patient is asleep or are of insufficient magnitude to trigger sufficient muscle contraction to achieve inhalation. In either case, the patient thereby fails to inhale until appropriate respiratory nerve signals are eventually generated—at which point fast, deep, rapid breathing occurs (i.e. hyperpnea) to compensate for the increased blood $CO_2$ levels arising due to the episode of CSA. In some cases, the episodes of CSA are fairly periodic and so periods of apnea alternate with periods of hyperpnea. In other words, a form of periodic breathing similar to CSR occurs. Note that, in the literature, CSR is sometimes classified as a type of CSA, regardless of the cause of the CSR. Herein, however, the term CSA is used to refer to the above-described neurogenic sleep disorder, which may or may not trigger periodic breathing.

In view of the significant adverse consequences of periodic breathing, particularly insofar as patients with CHF are concerned, it is highly desirable to provide techniques for detecting treating periodic breathing. Heretofore, periodic breathing therapy has been directed to improving respiration during the hypopnea/apnea phase. This may be achieved by, for example, applying diaphragmatic stimulation via phrenic nerve stimulation during the hypopnea/apnea phase using an implantable nerve stimulation system. The implantable nerve stimulation system may utilize a pacemaker or ICD as a controller to coordinate the detection of periodic breathing and the delivery of stimulation therapy in response thereto. Pacemakers and ICDs are usually implanted primarily for use in applying cardiac therapy for treating arrhythmias or for delivering cardiac resynchronization therapy (CRT) in an effort to alleviate CHF. However, many patients who are candidates for pacemakers or ICDs also suffer from CSR and hence could benefit from additional functionality directed to the detection and treatment of periodic breathing. Indeed, since periodic breathing can exacerbate CHF—yielding a higher risk of stroke or heart attack—CHF patients who would otherwise have pacemakers implanted therein could significantly benefit from periodic breathing therapy as well. An example of a technique for performing diaphragmatic stimulation during the hypopnea/apnea phase of periodic breathing using an implantable medical system incorporating a pacemaker is set forth in U.S. Pat. No. 6,415,183 to Scheiner et al., entitled "Method and Apparatus for Diaphragmatic stimulation."

With conventional diaphragmatic stimulation techniques, care should be taken to ensure that stimulation provided during the hypopnea/apnea phase does not inadvertently induce an upper airway occlusion due to decreased intrathoracic pressure caused by the diaphragmatic stimulation (i.e. decrease pressure relative to external air pressure.) In this regard, during normal respiration, the central nervous system provides stimulation signals to the phrenic nerves for contracting the diaphragm to induce respiration and simultaneously provides stimulation signals to muscles in the upper airway surrounding the respiration airway. Stimulation is provided by the central nervous system to increase muscle tone in the upper airway during inspiration by an amount to prevent collapse of the upper airway. However, with implantable stimulation systems, artificial stimulation may potentially be applied only to the phrenic nerves and not to the muscles surrounding the upper airway and so there is a risk that the upper airway will collapse during the artificially-induced respiration. This problem may be addressed by implanting additional stimulation devices for directly stimulating the muscles of the throat at the same time that the phrenic nerves are stimulated. Techniques are described in U.S. patent application Ser. No. 10/795,009 of Koh et al., entitled "System And Method For Distinguishing Among Obstructive Sleep Apnea, Central Sleep Apnea And Normal Sleep Using An Implantable Medical System", filed Mar. 3, 2004.

Although techniques such as Koh's for performing diaphragmatic stimulation during the hypopnea/apnea phase of periodic breathing are promising, it would be desirable to provide alternative techniques for treating periodic breathing using an implantable stimulation system and it is to that end that the present invention is primarily directed.

SUMMARY

In accordance with a first illustrative embodiment, techniques are provided for delivering therapy in response to periodic breathing within a patient using an implantable medical system, wherein diaphragmatic stimulation is delivered during periods of hyperpnea. In other words, rather than providing diaphragmatic stimulation during periods of hypopnea/apnea as is traditionally employed, the invention instead operates to apply diaphragmatic stimulation during hyperpnea. Preferably, the diaphragmatic stimulation is sufficient to decrease intrathoracic pressure during hyperpnea to the point that upper airway occlusion occurs, such that ventilation is reduced. Thus, whereas predecessor diaphragmatic stimulation techniques may seek to prevent upper airway occlusion, the technique of the invention instead operates to intentionally trigger just such an occlusion. By occluding the upper airway during hyperpnea, actual ventilation is thereby reduced during the hyperpnea phase of periodic breathing, thus reducing the cyclic blood chemistry imbalance that may sustain the periodic breathing. In one specific example, diaphragmatic stimulation is performed during hyperpnea using phrenic nerve stimulation in conjunction with a pacemaker or ICD, which operates to detect periodic breathing based upon thoracic impedance signals and to stimulate the phrenic nerve(s). The diaphragmatic stimulation is synchronized with intrinsic phrenic nerve signal bursts detected during hyperpnea (or inferred via thoracic impedance) so as to be properly synchronized with inhalation.

In accordance with a second illustrative embodiment, techniques are provided for delivering therapy in response to periodic breathing within a patient using an implantable medical system, wherein respiration is inhibited during periods of hyperpnea. Respiration may be inhibited by blocking intrinsic phrenic nerve signals. By inhibiting respiration during the hyperpnea phase of periodic breathing, actual ventilation is reduced during hyperpnea thus reducing the cyclic blood chemistry imbalance that may sustain periodic breathing. In one specific example, phrenic nerve signals are blocked by phrenic nerve inhibitors used in conjunction with a pacemaker or ICD, which operates to detect periodic breathing based upon thoracic impedance signals.

Additionally, in an exemplary implementation, the implanted system controls the type of therapy to be delivered based upon the severity of periodic breathing. If periodic breathing is relatively mild so that frank apnea does not occur, diaphragmatic stimulation is merely delivered during periods of hypopnea, in accordance with otherwise conventional techniques or in accordance with any suitable novel techniques. However, if periodic breathing is sufficiently severe such that frank apnea occurs, then therapy is instead delivered during the periods of hyperpnea—either in the form of diaphragmatic stimulation or phrenic nerve signal inhibition.

Thus, various techniques are provided for use with an implantable medical system for treating periodic breathing within a patient.

BRIEF DESCRIPTION OF THE DRAWINGS

The above and further features, advantages and benefits will be apparent upon consideration of the present description taken in conjunction with the accompanying drawings, in which.

DETAILED DESCRIPTION OF THE PREFERRED EMBODIMENTS

The following description includes the best mode presently contemplated. This description is not to be taken in a limiting sense but is made merely to describe general principles of the illustrative embodiments. The scope of the invention should be ascertained with reference to the issued claims. In the description that follows, like numerals or reference designators will be used to refer to like parts or elements throughout.

Overview of Implantable Periodic Breathing Treatment System

Figure 1:
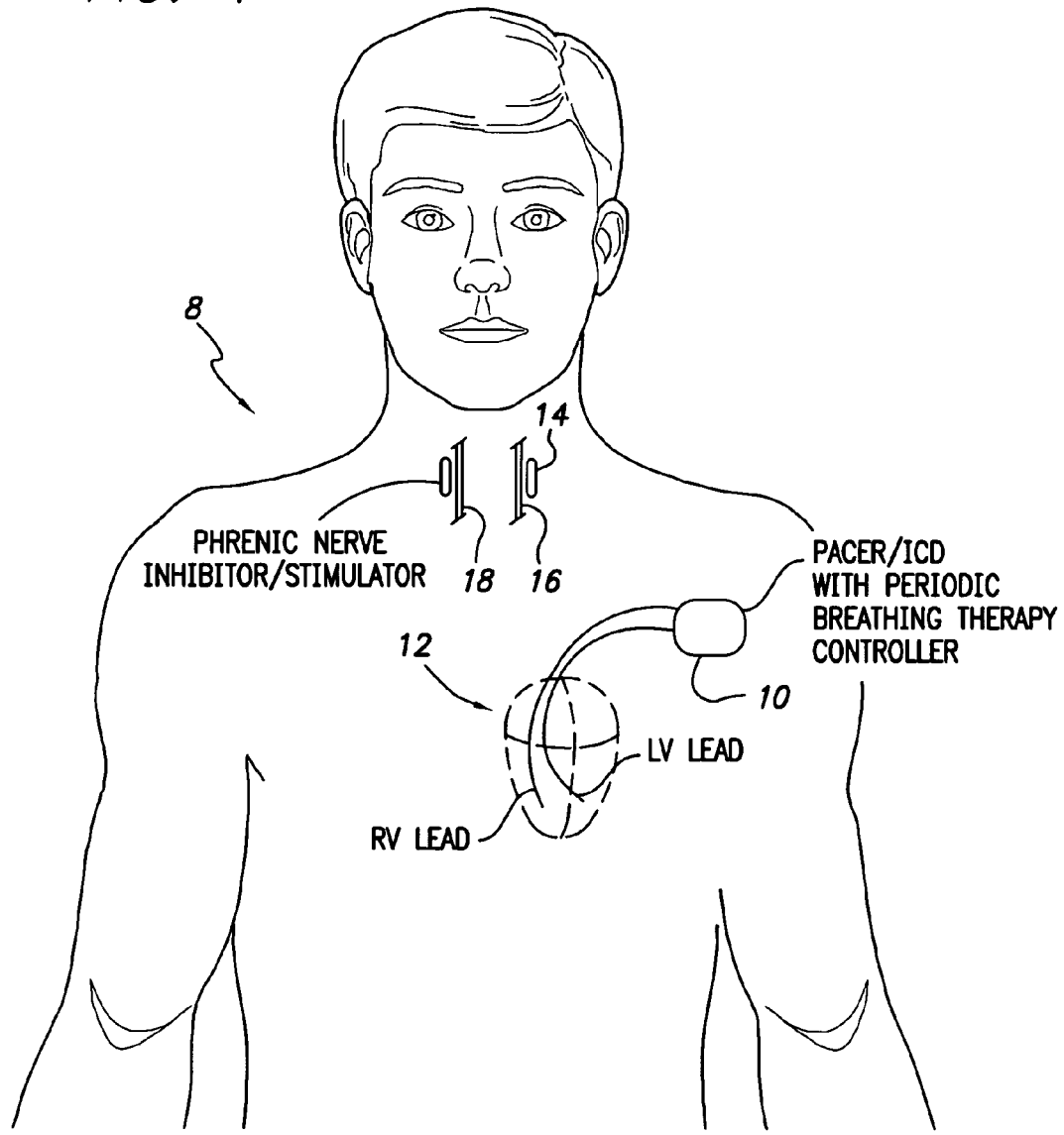
FIG. 1 illustrates pertinent components of an implantable periodic breathing treatment system having a pacemaker or ICD capable of detecting episodes of periodic breathing and delivering therapy in response thereto using phrenic nerve stimulator/inhibitors.
Figure 9:
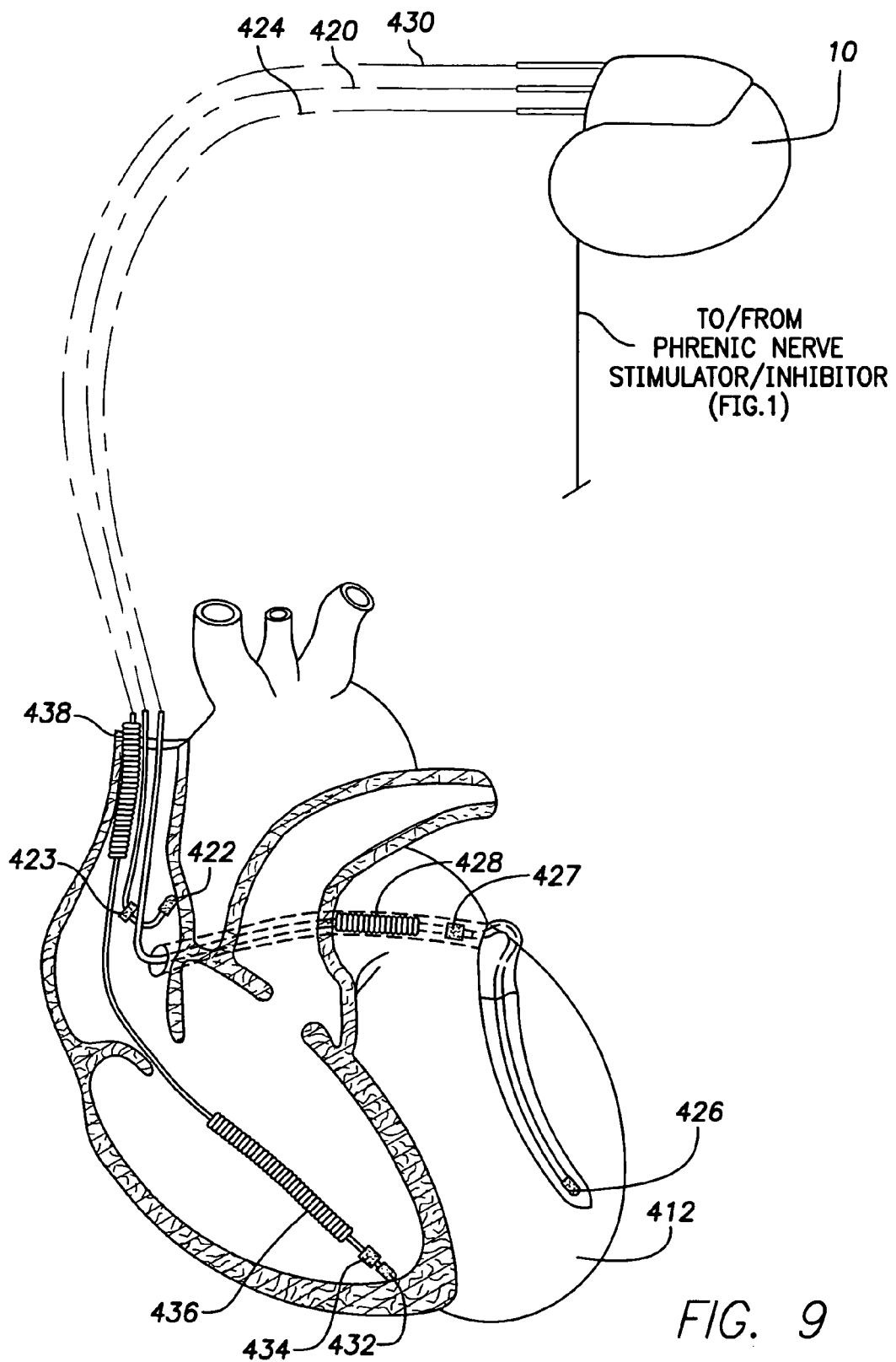
FIG. 9 is a simplified, partly cutaway view, illustrating the pacer/ICD of FIG. 1 along with at set of leads implanted into the heart of the patient.

FIG. 1 illustrates an implantable periodic breathing treatment system 8 capable of detecting periodic breathing and delivering therapy in response thereto. Periodic breathing treatment system 8 includes a pacer/ICD 10 or other cardiac stimulation device that incorporates internal components (shown in FIG. 10) for detecting periodic breathing and controlling delivery of therapy. To this end, pacer/ICD 10 receives impedance signals from various cardiac pacing leads 12, only two of which are shown in FIG. 1. A complete set of exemplary pacing leads are shown in FIG. 9. Based on the received impedance signals, the pacer/ICD monitors respiration and detects the onset of an episode of periodic breathing based on cyclic variations in respiration amplitudes indicative of alternating periods of hyperpnea and periods of hypopnea/apnea. To detect respiration via impedance derived from cardiac pacing leads, changes in respiration caused by the beating of the heart or other non-respiratory factors must be eliminated, which may be performed in accordance with otherwise conventional techniques. Other techniques may be employed for detecting periodic breathing as well, such as techniques exploiting variations in A-V delay or R-R oscillations. Periodic breathing detection techniques are set forth in U.S. Pat. No. 6,600,949 to Turcott, entitled "Method for Monitoring Heart Failure via Respiratory Patterns," and U.S. Pat. No. 6,589,188 to Street et al., entitled "Method for Monitoring Heart Failure via Respiratory Patterns".

Once an episode of periodic breathing has been detected, the system uses phrenic nerve stimulator/inhibitors 14 to treat the episode. To this end, the system either delivers diaphragmatic stimulation during hyperpnea phases of periodic breathing in accordance with techniques described below with reference to FIGS. 2 and 3 or inhibits intrinsic phrenic nerve signals during hyperpnea phases of periodic breathing in accordance with techniques described below with reference to FIG. 4. Additionally, or in the alternative, the system can evaluate the severity of the episode of periodic breathing, and then control the type of therapy to be delivered in accordance with techniques described below with reference to FIGS. 6-8.

For the sake of completeness, FIG. 1 illustrates a combined phrenic nerve stimulator/inhibitor. In many implementations, either phrenic nerve stimulators or phrenic nerve inhibitors will be implanted, but not both, depending upon the particular treatment technique to be employed. A combined phrenic nerve stimulator/inhibitor has the advantage of allowing a physician or other medical professional to control the type of periodic breathing therapy to be employed to best suit the needs of the patient. The combined stimulator/inhibitor may either be a single device capable of both nerve stimulation and inhibition or may comprise separate devices implanted at separate locations. The phrenic nerve stimulator/inhibitor is also preferably configured to sense intrinsic phrenic nerve signals. In the example of FIG. 1, phrenic nerve stimulator/inhibitors are shown implanted adjacent left and right phrenic nerves 16 and 18, respectively, in the upper thorax. This is merely illustrative. Phrenic nerves typically can be simulated or inhibited at any point along their path or after their innervation in the diaphragm. Note, however, that portions of the phrenic nerves pass epicardially over the heart and it may be disadvantageous to mount phrenic nerve stimulator/inhibitors adjacent to those portions of the phrenic nerves, since any electrical signals generated by the stimulator/inhibitors near the heart could potentially interfere with proper functioning of the heart.

Phrenic nerve stimulation devices are set forth in: U.S. Pat. No. 5,056,519 to Vince, entitled "Unilateral Diaphragmatic Pacer," and in the aforementioned patent to Scheiner et al. Other respiratory nerves may be stimulated as well. U.S. Pat. No. 5,911,218 to DiMarco, entitled "Method and Apparatus for Electrical Stimulation of the Respiratory Muscles to Achieve Artificial Ventilation in a Patient," describes stimulation of nerves leading to intercostal muscles. Nerve inhibition devices are discussed in: U.S. patent application 2002/0099256A1 of Manne, entitled "Electromagnetically Induced Anesthesia And Sensory Stimulation"; U.S. patent application 2002/0177882A1 of DiLorenzo, entitled "Optimal Method And Apparatus For Neural Modulation for the Treatment of Neurological Disease, Particularly Movement Disorders"; U.S. patent application 2003/0045914A1 of Cohen et al., entitled "Treatment Of Disorders By Unidirectional Nerve Stimulation"; U.S. patent application 2003/0216792A1 of Levin et al., entitled "Renal Nerve Stimulation Method And Apparatus for Treatment of Patients"; U.S. Pat. No. 5,755,750 to Petruska, et al., entitled Method and Apparatus for Selectively Inhibiting Activity in Nerve Fibers."

Thus, FIG. 1 provides an overview of an implantable system for detecting periodic breathing and for delivering therapy in response thereto. Internal signal transmission lines for interconnecting the various implanted components are not shown. Alternatively, wireless signal transmission may be employed. The particular locations of the implanted components are merely exemplary.

Diaphragmatic Stimulation During Hyperpnea

Figure 2:
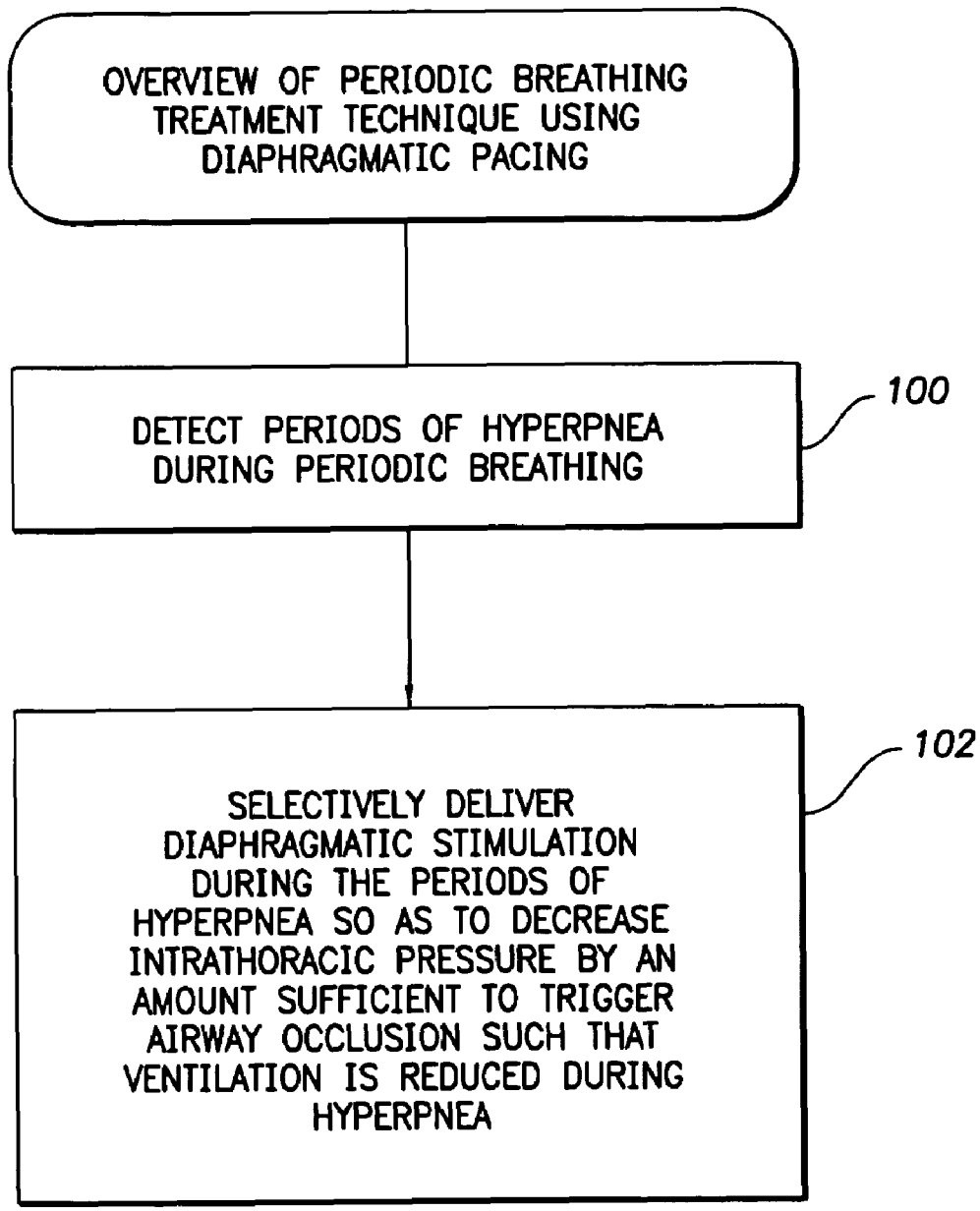
FIG. 2 is a flow diagram providing an overview of a technique for treating periodic breathing via diaphragmatic stimulation during hyperpnea, which can be performed by the system of FIG. 1.
Figure 3:
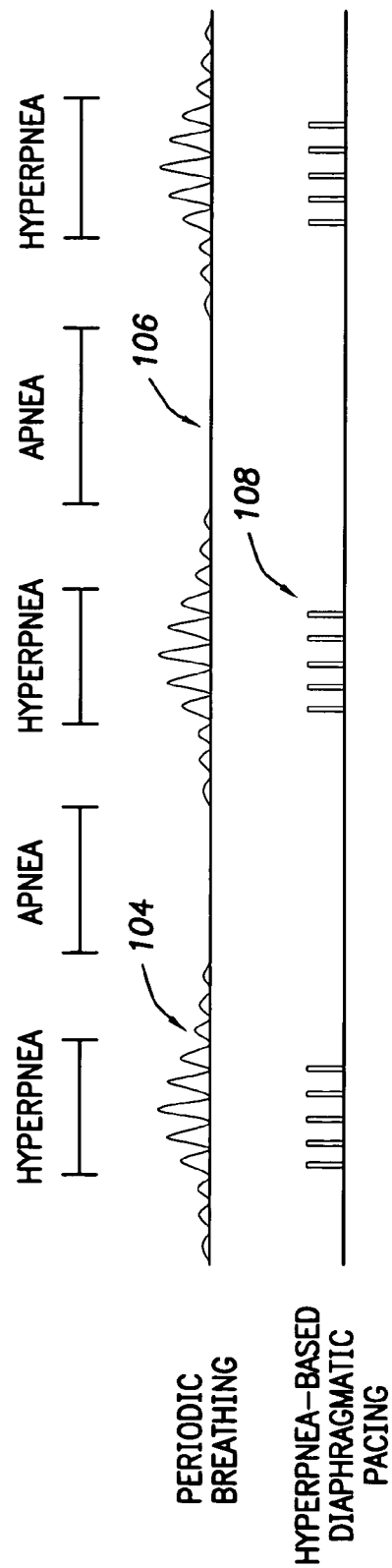
FIG. 3 is a stylized diagram of episodes of periodic breathing, particularly illustrating periods of hyperpnea during which diaphragmatic stimulation is delivered in accordance with the technique of FIG. 2.

FIG. 2 provides an overview of the hyperpnea-based diaphragmatic stimulation techniques according to at least one illustrative embodiment. Initially, at step 100, the implantable pacer/ICD detects periods of hyperpnea during periodic breathing. Then, at step 102, the pacer/ICD delivers diaphragmatic stimulation during periods of hyperpnea so as to decrease intrathoracic pressure by an amount sufficient to trigger airway occlusion such that ventilation is reduced during hyperpnea. This is illustrated in FIG. 3, which provides a stylized representation of exemplary periodic breathing and diaphragmatic stimulation. In the example, periodic bursts of heavy, deep breathing (i.e. hyperpnea) 104 alternate with periods of frank apnea 106. This form of periodic breathing often occurs during CSR. Note that hyperpnea refers only to respiration amplitudes in excess of what would otherwise be normal. With CSR, there is often some respiration occurring between the hypopnea and hyperpnea phases that is within a more or less normal amplitude range. Such respiration is not classified as either hyperpneic or hypopneic.

Diaphragmatic stimulation 108 is provided during the periods of hyperpnea by stimulating the phrenic nerves during inspiration portions of intrinsic respiration cycles, i.e. the diaphragmatic stimulation signals are synchronized with intrinsic bursts of phrenic nerve signals generated by the central nervous system. By synchronizing diaphragmatic stimulation with intrinsic phrenic nerve signals (not separately shown), the intrinsic phrenic nerve signals are thereby augmented thus producing an increase in ventilatory amplitude, i.e. the diaphragm is thereby stimulated to contract more vigorously. The stimulation applied to the phrenic nerves leading to the diaphragm may be augmented with stimulation applied to other nerves leading to other muscles involved in respiration, such as the intercostal muscles. To achieve synchronous stimulation, the pacer/ICD may monitor patient respiration via changes in thoracic impedance to detect periods of inspiration. Alternatively, if a phrenic nerve signal sensor is provided, the pacer/ICD may use the sensor to directly detect bursts of phrenic nerve signals associated with inspiration to allow synchronization of stimulation with the intrinsic signals.

By augmenting intrinsic phrenic nerve signals during the hyperpnea phases of periodic breathing using diaphragmatic stimulation, intrathoracic pressure is caused to decrease during hyperpnea, tending to produce upper airway occlusion. As noted above, during normal respiration, the central nervous system sends nerve signals to muscles surrounding the upper airway during inspiration to increase muscle tone so as to prevent any collapse or occlusion of the respiration airway. The intensity of these nerve signals is generally proportional to the intensity of phrenic nerve signal bursts sent to the diaphragm so that, the deeper the inhalation, the greater the increase in muscle tone surrounding the upper airway. However, by augmenting the intrinsic phrenic nerve signals with diaphragmatic stimulation, the diaphragm contracts downwardly by a greater amount, thus reducing intrathoracic pressure more so than would otherwise be achieved. The resultant additive reduction in intrathoracic pressure is unaccounted for by the central nervous system leading to possible upper airway occlusion. If airway occlusion is achieved, then actual ventilation is reduced. In other words, although the diaphragm contracts deeply during hyperpnea phase, little or no air actually reaches the lungs. By limiting the amount of air that reaches the lungs, the above-described cycle that perpetuates periodic breathing, particularly CSR, may be broken or at least reduced in severity.

Note that, although synchronous diaphragmatic stimulation is preferred, asynchronous stimulation may instead be employed in some cases. With asynchronous stimulation, at least some phrenic nerve stimulation is delivered during exhalation, likely triggering an immediate and significant occlusion of the airway sufficient to awaken the patient. This may be desirable for any episodes of periodic breathing where synchronous diaphragmatic stimulation is not sufficient to prevent frank apnea from occurring. In such cases, it may be desirable to employ asynchronous diaphragmatic stimulation to immediately awaken the patient, thus terminating periodic breathing and thereby preventing extended periods of frank apnea, which could exacerbate medical conditions, such as CHF.

Finally, with regard to FIG. 3, note that the periodic breathing respiration pattern shown therein is a stylized pattern provided to clearly illustrate the cyclic nature of the respiration pattern and should not be construed as representing an actual clinically-detected respiration pattern. In addition, the respiration pattern shown therein is representative of the intrinsic respiration pattern that arises in the absence of any artificial diaphragmatic stimulation. Artificial diaphragmatic stimulation will disrupt the intrinsic respiration pattern resulting, ultimately, in increased respiration amplitudes during the hypopnea phases. Once respiration amplitudes increase during hypopnea phases, any diaphragmatic stimulation applied during hyperpnea phases is preferably reduced or eliminated. In one example described below, diaphragmatic stimulation is only provided during hyperpnea if the episode of periodic breathing is sufficiently severe to trigger periods of frank apnea. For comparatively mild episodes of periodic breathing without frank apnea, diaphragmatic stimulation is instead applied during hypopnea.

Thus, FIGS. 2-3 provide an overview of the hyperpnea-based diaphragmatic stimulation techniques according to at least one illustrative embodiment. In the following, an overview of hyperpnea-based respiration inhibition techniques is provided.

Respiration Inhibition During Hyperpnea

Figure 4:
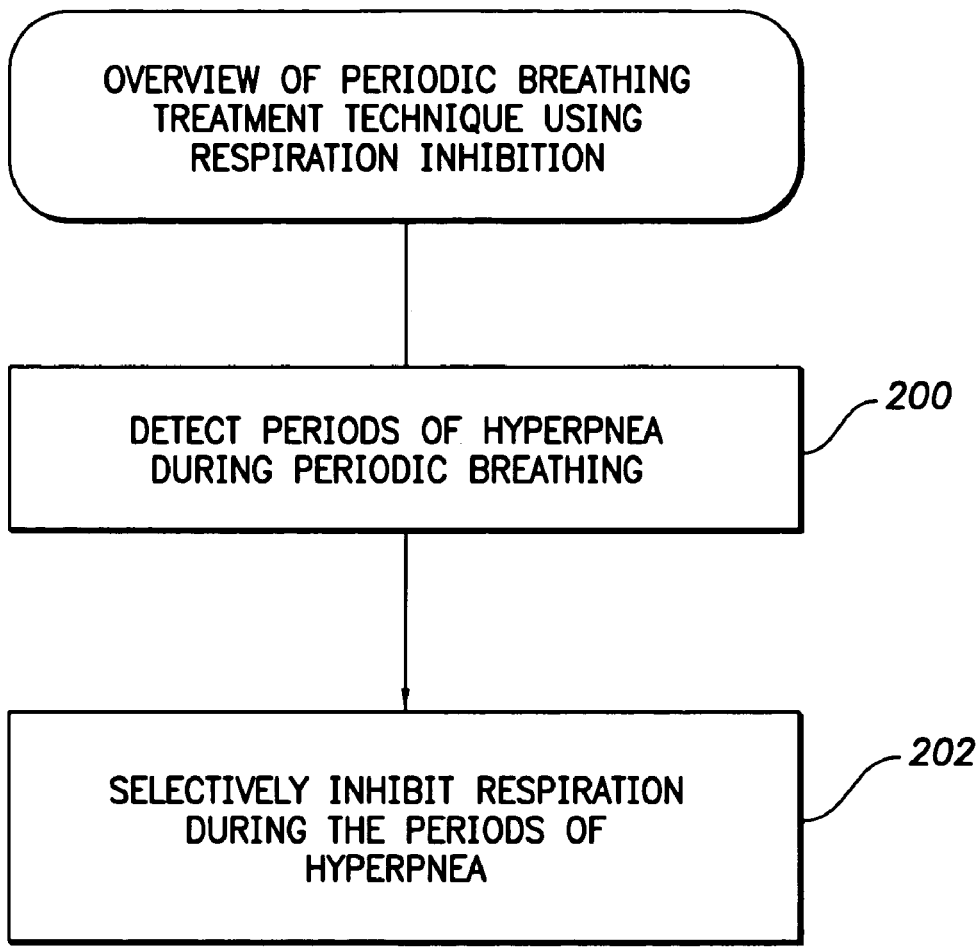
FIG. 4 is a flow diagram providing an overview of a technique for treating periodic breathing via the inhibition of phrenic nerve signals during hyperpnea, which can be performed by the system of FIG. 1.
Figure 5:
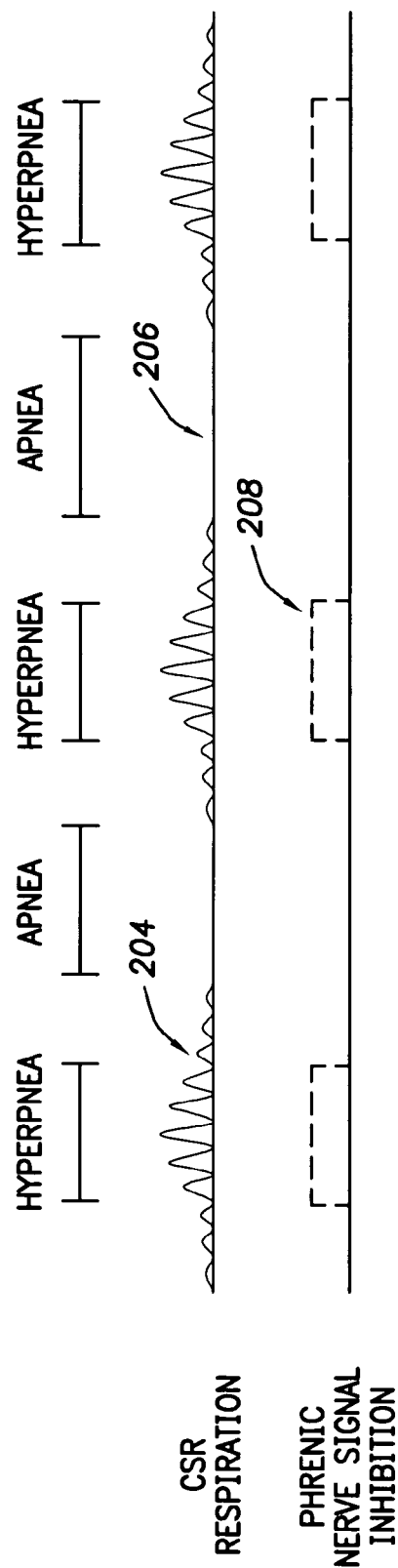
FIG. 5 is a stylized diagram of episodes of periodic breathing, particularly illustrating periods of hyperpnea during which respiration is inhibited in accordance with the technique of FIG. 4.

FIG. 4 provides an overview of the hyperpnea-based respiration inhibition techniques according to one illustrative embodiment. As before, at step 200, the implantable pacer/ICD detects periods of hyperpnea during periodic breathing. However, at step 202, rather than providing diaphragmatic stimulation via the phrenic nerves, the pacer/ICD instead controls a phrenic nerve inhibitor (or similar device) to selectively inhibit respiration during the periods of hyperpnea. This is illustrated in FIG. 5, which provides a stylized representation of periodic breathing characterized by hyperpnea phases 204 separated by hypopnea phases 206. Phrenic nerve signal inhibition 208 is provided during each of the periods of hyperpnea by inhibiting intrinsic nerve signal propagation along the phrenic nerves either during the entire hyperpnea phase (as shown) or during selected portions of the hyperpnea phase. By inhibiting intrinsic phrenic nerve signal propagation during the hyperpnea phase, actual ventilation is reduced. In other words, although the central nervous system sends out phrenic nerve signals intending to cause the diaphragm to contract deeply during the hyperpnea phase, reduced respiration amplitudes instead occur. By limiting respiration during hyperpnea, the above-described cycle that may perpetuate periodic breathing is broken or at least reduced in severity.

The specific form of phrenic nerve signal inhibition depends upon the particular type of inhibitory device used. For devices capable of completely blocking phrenic nerve signals, it may be desirable to selectively activate and deactivate inhibition during the hyperpnea phase so as to modulate the amount of actual respiration to achieve a relatively normal level of respiration. For example, only every other intrinsic respiration cycle may be permitted to occur. For devices capable of only reducing nerve signal activity, it may be desirable to instead operate the inhibition device throughout the entire period of hyperpnea to achieve a reduction in ventilation amplitude for each respiration cycle. In either case, overall ventilation is thereby reduced. Note nerve signals leading to other muscles involved in respiration, such as the intercostal muscles, may also be inhibited.

Finally with regard to FIG. 5, as with FIG. 3, the periodic breathing respiration pattern shown therein is merely a stylized pattern provided illustrate the cyclic nature of the periodic breathing and should not be construed as representing an actual clinically-detected respiration pattern. The respiration pattern shown therein is representative of the intrinsic periodic breathing pattern that arises in the absence of any respiration inhibition. With respiration inhibition activated during hyperpnea, respiratory amplitudes will be reduced during hyperpnea. Ultimately, the reduction in respiration during hyperpnea will likely serve to disrupt the cycle that sustains the periodic breathing, resulting in increased respiration during the hypopnea phases. Once respiration increases during the hypopnea phases, respiration inhibition during the hyperpnea phases is then reduced or eliminated. Preferably, respiration inhibition is only provided to the extent necessary to reduce or eliminate periodic breathing. In an example described below, respiratory inhibition is only provided during hyperpnea if the episode of periodic breathing is sufficiently severe to trigger periods of frank apnea. For comparatively mild episodes of periodic breathing without frank apnea, diaphragmatic stimulation is instead applied during hypopnea.

Thus, FIGS. 4-5 provide an overview of the hyperpnea-based respiration inhibition techniques. In the following, an exemplary embodiment is described wherein hyperpnea-based periodic breathing treatment techniques are only activated during episodes of periodic breathing sufficiently severe to trigger frank apnea.

Severity-Based Treatment Example

Figure 6:
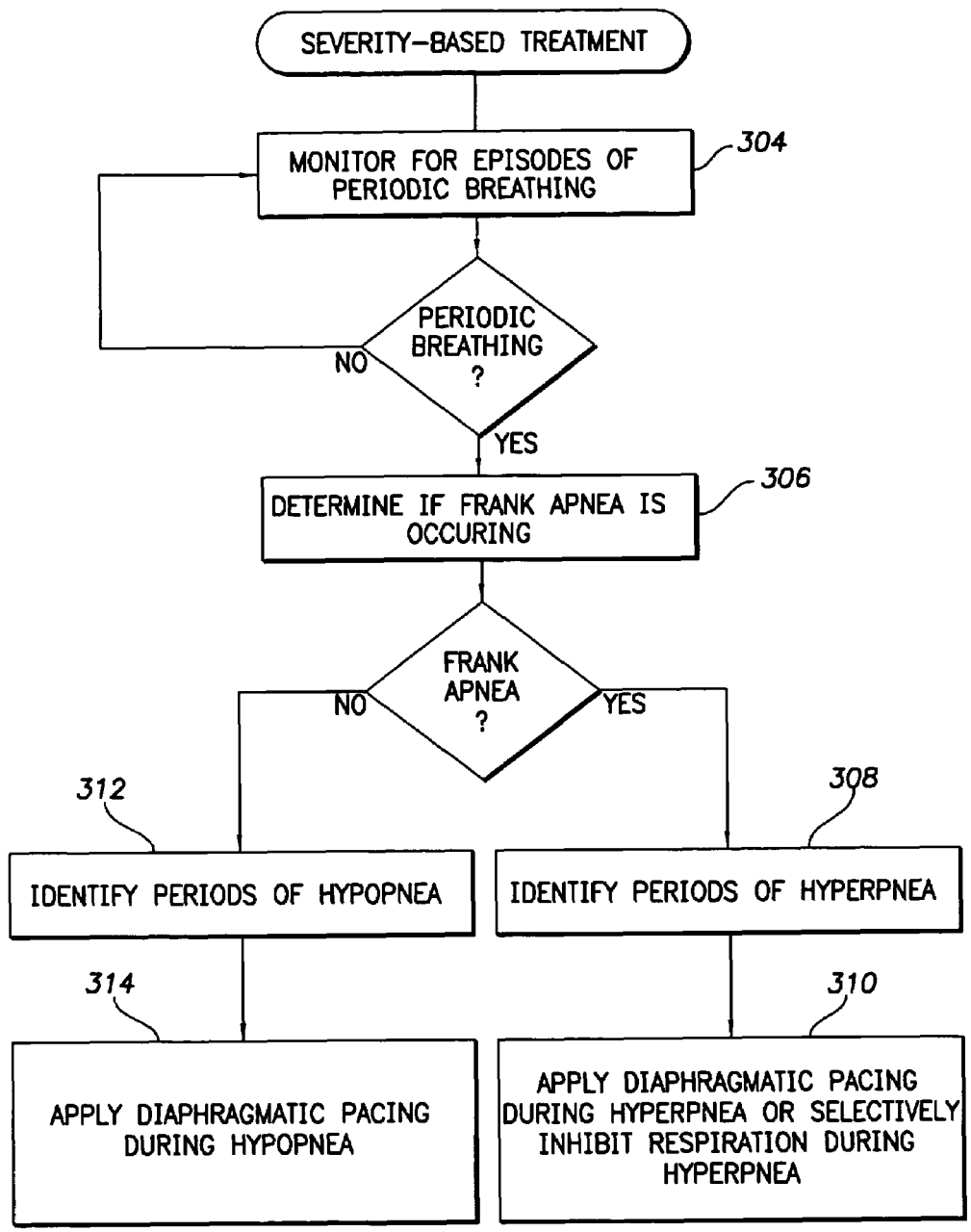
FIG. 6 is a flow diagram providing an overview of an exemplary method for treating periodic breathing using the various techniques of FIGS. 2-5 but wherein the type of treatment depends upon the severity of periodic breathing.

FIG. 6 provides an overview of a periodic breathing treatment technique wherein the hyperpnea-based diaphragmatic stimulation techniques (or respiration inhibition techniques) described above are activated only if frank apnea occurs; otherwise conventional hypopnea-based diaphragmatic stimulation is instead employed. Briefly, beginning at step 304, the pacer/ICD monitors for episodes of periodic breathing. Periodic breathing may be detected, for example, based on an examination of intrinsic phrenic nerve signals, if any, sensed via devices 14 of FIG. 1, or based on patterns exhibited in thoracic impedance signals sensed via leads 12 of FIG. 1, or using any other suitable detection technique. If periodic breathing is detected then, at step 306, the pacer/ICD evaluates the severity of the episode periodic breathing, i.e. the pacer/ICD determines whether frank apnea is occurring. In one example, frank apnea is detected based on a complete absence of intrinsic phrenic nerve signals over some predetermined period of time, perhaps, thirty seconds.

If frank apnea is detected, then steps 308 and 310 are then performed wherein the pacer/ICD identifies periods of hyperpnea then either (1) applies diaphragmatic stimulation in accordance with the techniques of FIGS. 2-3 or inhibits respiration in accordance with the techniques of FIGS. 4-5. If frank apnea is not detected, then steps 312 and 314 are instead performed wherein the pacer/ICD identifies periods of hypopnea (which may include periods of non-frank apnea) and applies diaphragmatic stimulation during the hypopnea, in accordance with otherwise conventional techniques. In this regard, the phrenic nerve stimulators of FIG. 1 may be employed to provide phrenic nerve stimulation during the periods of hypopnea. Any diaphragmatic stimulation provided either during hyperpnea or during hypopnea is preferably synchronized with intrinsic inhalation, as shown.

Figure 7:
FIG. 7 is a stylized diagram of episodes of severe periodic breathing involving frank apnea, wherein diaphragmatic stimulation is employed during periods of hyperpnea in accordance with the technique of FIG. 6.
Figure 8:
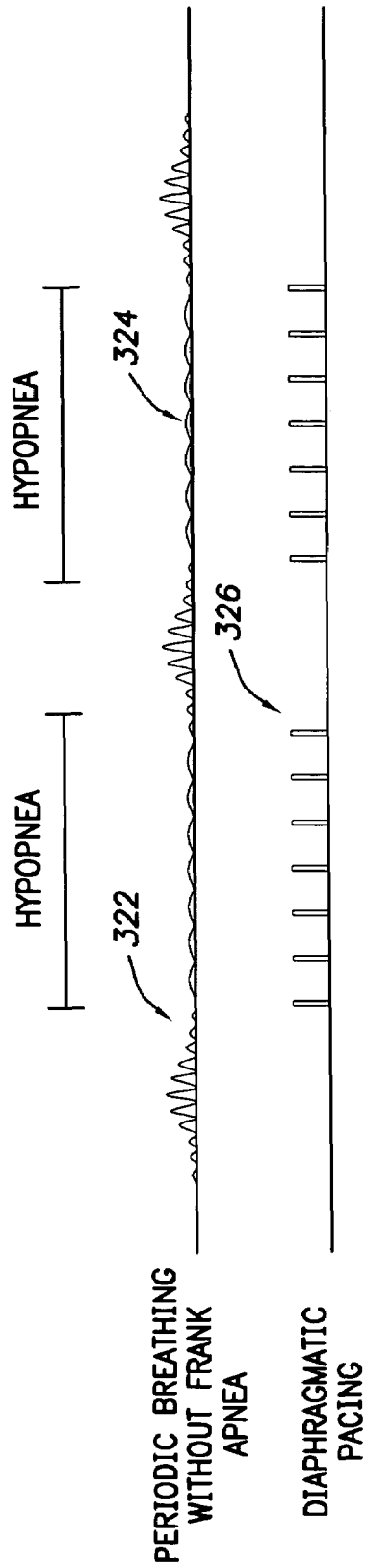
FIG. 8 is a stylized diagram of episodes of comparatively mild periodic breathing, wherein diaphragmatic stimulation is employed during periods of hypopnea also in accordance with the technique of FIG. 6.

The severity-based technique is illustrated in FIGS. 7-8. Briefly, FIG. 7 illustrates a severe periodic breathing respiration pattern with alternating phases of profound hyperpnea 316 and frank apnea 318. FIG. 7 also illustrates delivery of synchronous diaphragmatic stimulation 320 during the hyperpnea phases. Alternatively, instead of providing diaphragmatic stimulation during hyperpnea, respiration inhibition may instead be performed during the periods of hyperpnea, using the techniques described above. Turning now to FIG. 8, a comparatively mild periodic breathing respiration pattern is shown having alternating phases of mild hyperpnea 322 and mild hypopnea 324, with the latter characterized by shallow breathing. FIG. 8 also illustrates delivery of synchronous diaphragmatic stimulation 326 during the hypopnea phases.

Thus, with the technique of FIGS. 6-8, otherwise conventional diaphragmatic stimulation techniques are employed during periods of hypopnea if periodic breathing is relatively mild; whereas hyperpnea-based diaphragmatic stimulation or respiration inhibition is instead performed when periodic breathing is sufficiently severe such that frank apnea occurs. Alternatively, the evaluation of the degree of severity of periodic breathing may be further refined to allow for additional levels of therapy. For example, the duration episodes of frank apnea may be evaluated, with longer durations being associated with more severe periodic breathing. Aggressive hyperpnea-based therapy is applied for the most severe forms of periodic breathing having the longest episodes of apnea; less aggressive hyperpnea-based therapy is applied for less severe periodic breathing having shorter episodes of apnea; and hypopnea-based therapy is applied for periodic breathing where frank apnea does not occur. The aggressiveness of hyperpnea-based therapy may be controlled, for example, by controlling the intensity of phrenic nerve stimulation. Preferably, the pacer/ICD is configured to allow a physician or other medical professional to select the type of therapy to the employed and its aggressiveness, so as the best serve the needs of individual patients.

For the sake of completeness, a description of an exemplary pacer/ICD will now be provided. As many patients who suffer from periodic breathing are also candidates for pacer/ICDs, it is advantageous to configure a pacer/ICD to serve as the controller of the implantable periodic breathing treatment system. These techniques, however, may be performed using any suitable implantable components.

Exemplary Pacer/ICD

Figure 10:
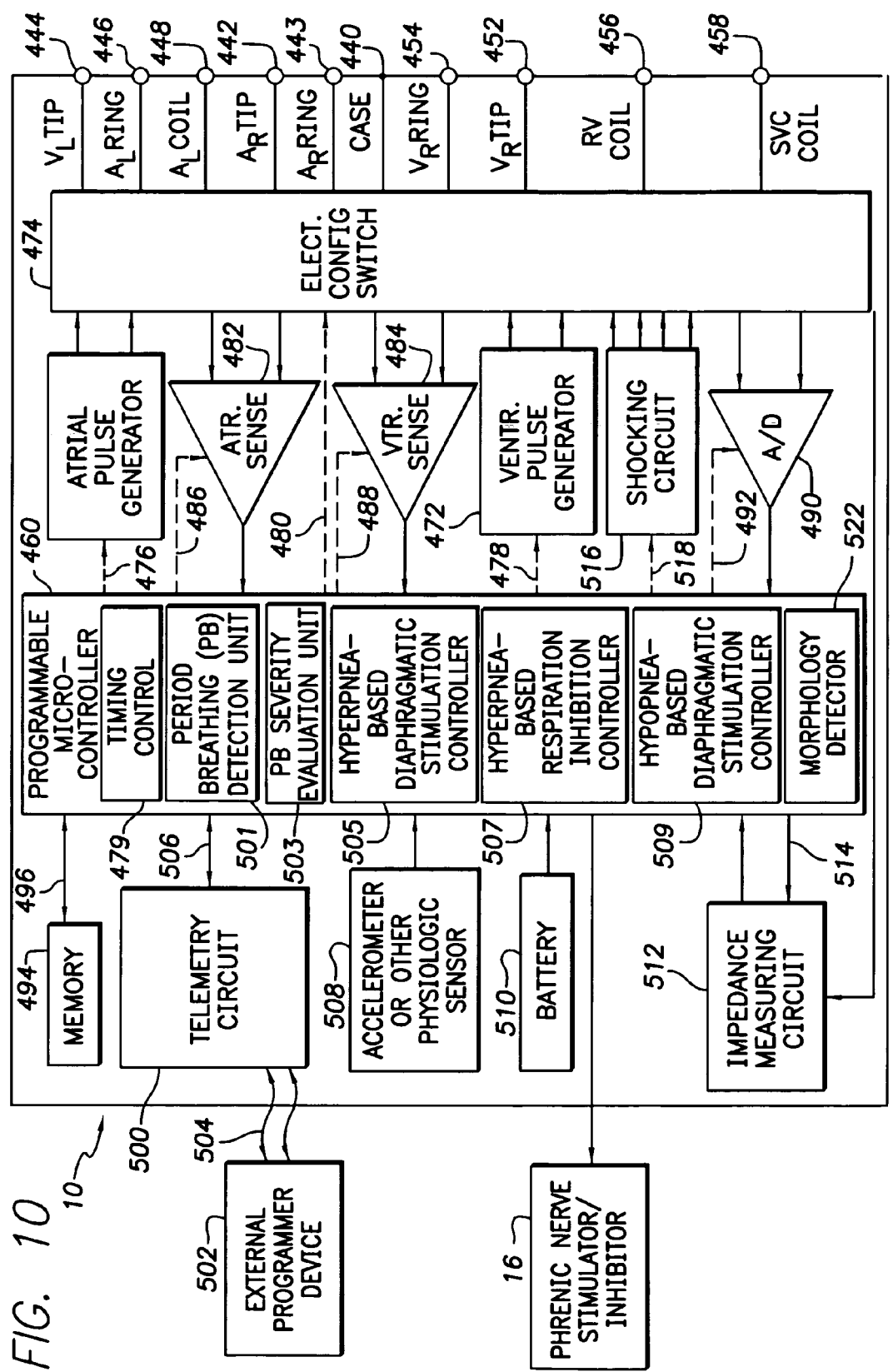
FIG. 10 is a functional block diagram of the pacer/ICD of FIG. 9, illustrating basic circuit elements that provide cardioversion, defibrillation and/or pacing stimulation in four chambers of the heart and particularly illustrating components for treating periodic breathing.

With reference to FIGS. 9 and 10, a description of the pacer/ICD of FIG. 1 will now be provided. FIG. 9 provides a simplified block diagram of the pacer/ICD, which is a dual-chamber stimulation device capable of treating both fast and slow arrhythmias with stimulation therapy, including cardioversion, defibrillation, and pacing stimulation, as well as capable of detecting periodic breathing, evaluating its severity, and controlling delivering of periodic breathing therapy in response thereto.

To provide atrial chamber pacing stimulation and sensing, pacer/ICD 10 is shown in electrical communication with a heart 412 by way of a left atrial lead 420 having an atrial tip electrode 422 and an atrial ring electrode 423 implanted in the atrial appendage. Pacer/ICD 10 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 424 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 9, it should also be understood that additional stimulation leads (with one or more pacing, sensing and/or shocking electrodes) might be used in order to efficiently and effectively provide pacing stimulation to the left side of the heart or atrial cardioversion and/or defibrillation.

A simplified block diagram of internal components of pacer/ICD 10 is shown in FIG. 10. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 440 for pacer/ICD 10, shown schematically in FIG. 10, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial tip electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 432, right ventricular ring electrode 434, the RV coil electrode 436, and the SVC coil electrode 438, respectively.

At the core of pacer/ICD 10 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical. Rather, any suitable microcontroller 460 may be used that carries out the functions described herein. The use of microprocessor-based control circuits for performing timing and data analysis functions are well known in the art.

As shown in FIG. 10, an atrial pulse generator 470 and a ventricular pulse generator 472 generate pacing stimulation pulses for delivery by the right atrial lead 420, the right ventricular lead 430, and/or the coronary sinus lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 482 and ventricular sensing circuits 484 may also be selectively coupled to the right atrial lead 420, coronary sinus lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 10 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the coronary sinus lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 10 (as contained in the microcontroller 460 or memory 494) to be sent to the external device 502 through an established communication link 504. Pacer/ICD 10 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV Delay, V-V Delay, etc.) at which the atrial and ventricular pulse generators, 470 and 472, generate stimulation pulses. While shown as being included within pacer/ICD 10, it is to be understood that the physiologic sensor 508 may also be external to pacer/ICD 10, yet still be implanted within or carried by the patient. A common type of rate responsive sensor is an activity sensor incorporating an accelerometer or a piezoelectric crystal, which is mounted within the housing 440 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG. 10. The battery 510 may vary depending on the capabilities of pacer/ICD 10. If the system only provides low voltage therapy, a lithium iodine or lithium copper fluoride cell may be utilized. For pacer/ICD 10, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 10 is preferably capable of high voltage therapy and appropriate batteries.

As further shown in FIG. 10, pacer/ICD 10 is shown as having an impedance measuring circuit 512 which is enabled by the microcontroller 460 via a control signal 514. Herein, thoracic impedance is primarily detected for use in tracking thoracic respiratory oscillations. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

Microcontroller 460 also includes various components directed to the detection, evaluation and treatment of periodic breathing. More specifically, the microcontroller includes a periodic breathing detection unit 501 and a periodic breathing severity evaluation unit 503. Periodic breathing detection is performed in accordance with techniques described above with reference to FIG. 1. Periodic breathing severity evaluation is performed in accordance with techniques described above with reference to FIG. 6. A hyperpnea-based diaphragmatic stimulation controller 505 operates, in accordance with techniques described above with reference to FIGS. 2-3, to deliver diaphragmatic stimulation during hyperpnea phases of periodic breathing via phrenic nerve stimulator/inhibitor 16, operating in a stimulation mode. A hyperpnea-based respiration inhibition controller 507 operates, in accordance with techniques the described above with reference to FIGS. 4-5, to inhibit respiration during hyperpnea phases of periodic breathing using phrenic nerve stimulator/inhibitor 16, operating in an inhibition mode. Finally, a hypopnea-based diaphragmatic stimulation controller 509 operates, in accordance with techniques described above with reference to FIGS. 6-8, to deliver diaphragmatic stimulation during hypopnea phases of mild periodic breathing via phrenic nerve stimulator/inhibitor 16, operating in the stimulation mode. Preferably, the hypopnea-based controller operates to deliver therapy only during episodes of periodic breathing that do not include frank apnea (as determined by periodic breathing severity evaluation unit 503.) If periodic breathing is deemed to be severe (i.e. frank apnea occurs) then, depending upon the programming of the pacer/ICD, either the hyperpnea-based diaphragmatic stimulation controller operates to delivery of diaphragmatic stimulation during periods of hyperpnea or the hyperpnea-based respiration inhibition controller operates to apply phrenic nerve inhibition during periods of hyperpnea. In many implementations, not all of these components will be provided. For example, the pacer/ICD may be provided with either the hyperpnea-based diaphragmatic stimulation controller or the hyperpnea-based respiration inhibition controller, but not both, depending upon whether a phrenic nerve stimulator or a phrenic nerve inhibitor is provided. In addition, the hypopnea-based diaphragmatic stimulation controller is optional and is preferably provided only if a phrenic nerve stimulator is employed.

Finally, although several of these internal components are shown as being sub-components of the microcontroller, some or all may be implemented separately from the microcontroller. Depending upon the implementation, the various components of the microcontroller may be separate software modules. The modules may be combined so as to permit a single module to perform multiple functions.

What have been described are various systems and methods for treating periodic breathing using an implantable system controlled by a pacer or ICD. However, other implantable systems or techniques may be used. Thus, while particular exemplary embodiments have been described, modifications can be made thereto without departing from the spirit and scope of the invention.

What is claimed is:

1. A method for delivering therapy in response to periodic breathing within a patient using an implantable medical system, the method comprising:
    detecting a period of hyperpnea; and
    selectively delivering diaphragmatic stimulation during the period of hyperpnea.

2. The method of claim 1 wherein the diaphragmatic stimulation is delivered by an amount sufficient to cause upper airway occlusion such that actual ventilation is reduced during the periods of hyperpnea so as to mitigate periodic breathing.

3. The method of claim 1 wherein the diaphragmatic stimulation is synchronized with intrinsic respiration occurring during hyperpnea.

4. The method of claim 1 wherein the diaphragmatic stimulation is delivered in response to periods of hyperpnea occurring during Cheyne-Stokes Respiration.

5. The method of claim 1 wherein an implantable nerve stimulator is provided and wherein delivering diaphragmatic stimulation during hyperpnea is performed by delivering electrical nerve stimulation to the phrenic nerves of the patient using the implantable nerve stimulator.

6. The method of claim 1 further comprising determining whether frank apnea is occurring during the hypopnea periods of the periodic breathing and wherein diaphragmatic stimulation is delivered during the periods of hyperpnea only if frank apnea is found to occur during the during the hypopnea periods.

7. An implantable medical system for delivering therapy in response to periodic breathing within a patient, the system comprising:
    a periodic breathing detection system operative to detect episodes of periodic breathing and to identify periods of hyperpnea therein; and
    a hyperpnea-based diaphragmatic stimulation system operative to selectively deliver diaphragmatic stimulation during the periods of hyperpnea.

8. The implantable medical system of claim 7 wherein the diaphragmatic stimulation system is operative to deliver diaphragmatic stimulation in an amount sufficient to cause upper airway occlusion.

9. The implantable medical system of claim 7 wherein the diaphragmatic stimulation system is operative to synchronize the diaphragmatic stimulation with intrinsic respiration.

10. The implantable medical system of claim 7 wherein the periodic breathing detection system is operative to detect Cheyne-Stokes Respiration, and wherein the diaphragmatic stimulation system is operative to deliver diaphragmatic stimulation in response to periods of hyperpnea occurring during Cheyne-Stokes Respiration.

11. The implantable medical system of claim 7 wherein the diaphragmatic stimulation system comprises an implantable nerve stimulator that is operative to deliver electrical nerve stimulation to the phrenic nerves of the patient.

12. An implantable medical system for delivering therapy in response to periodic breathing within a patient, the system comprising:
    a periodic breathing detection system operative to detect episodes of periodic breathing and to identify periods of hyperpnea and hypopnea therein;
    a periodic breathing severity evaluation system operative to detect episodes of frank apnea, if any, occurring during the periods of hypopnea;
    a hyperpnea-based diaphragmatic stimulation system operative to selectively deliver diaphragmatic stimulation during the periods of hyperpnea if frank apnea is found to occur during the periods of hypopnea; and
    a hypopnea-based diaphragmatic stimulation system operative to selectively deliver diaphragmatic stimulation during the periods of hypopnea if frank apnea is not found to occur during the periods of hypopnea.

13. The implantable medical system of claim 12 wherein the diaphragmatic stimulation system is operative to deliver diaphragmatic stimulation in an amount sufficient to cause upper airway occlusion.

14. The implantable medical system of claim 12 wherein the diaphragmatic stimulation system is operative to synchronize the diaphragmatic stimulation with intrinsic respiration.

15. The implantable medical system of claim 12 wherein the periodic breathing detection system is operative to detect Cheyne-Stokes Respiration, and wherein the diaphragmatic stimulation system is operative to deliver diaphragmatic stimulation in response to periods of hyperpnea occurring during Cheyne-Stokes Respiration.

16. The implantable medical system of claim 12 wherein the diaphragmatic stimulation system comprises an implantable nerve stimulator that is operative to deliver electrical nerve stimulation to the phrenic nerves of the patient.

* * * * *